United States Patent [19]

Flack et al.

[11] 4,258,709

[45] Mar. 31, 1981

[54] DEVICE TO COMBAT DRIBBLING

[75] Inventors: Frederick C. Flack; Richard E. Ellis, both of Exeter; Kenneth Bundy, Dawlish; Francis Miners; Wilfred G. Selley, both of Exeter, all of England

[73] Assignee: University of Exeter, Devon, England

[21] Appl. No.: 23,600

[22] Filed: Mar. 26, 1979

[30] Foreign Application Priority Data

Mar. 29, 1978 [GB] United Kingdom ............... 12301/78

[51] Int. Cl.³ .............................................. A61F 5/00
[52] U.S. Cl. .................................. 128/136; 340/573
[58] Field of Search ............. 128/135, 136, 164, 777, 128/787, 908; 340/573, 575

[56] References Cited

U.S. PATENT DOCUMENTS

| 1,967,815 | 7/1934 | Frieberg | 128/787 |
| 3,054,868 | 9/1962 | Phillians | 340/575 X |
| 3,363,242 | 1/1968 | Currey et al. | 340/575 |
| 3,508,235 | 4/1970 | Baisden | 340/573 X |
| 3,699,432 | 10/1972 | Brown | 128/908 X |
| 3,720,209 | 3/1973 | Bolduc | 128/908 X |

FOREIGN PATENT DOCUMENTS

| 257976 | 6/1912 | Fed. Rep. of Germany . | |
| 743034 | 1/1944 | Fed. Rep. of Germany . | |
| 1038829 | 8/1966 | United Kingdom | 128/787 |
| 1246370 | 9/1971 | United Kingdom . | |
| 1418006 | 12/1975 | United Kingdom . | |
| 1472067 | 4/1977 | United Kingdom . | |

*Primary Examiner*—Kyle L. Howell
*Attorney, Agent, or Firm*—Larson, Taylor and Hinds

[57] ABSTRACT

A device for teaching a patient to keep his lips closed, to combat dribbling, has a sensor electrode (12,22,46) for insertion between the lips, and an electrical detector (G1) and indicator (30) to indicate cessation of contact with at least one lip. The patient is thus reminded to keep his lips closed.

In one form, there is a secondary electrode (26) attached to a remote part of the patient's body, the detector detecting when an electrical circuit through the body is broken by the sensor electrode falling from the lips. In another form, the sensor electrode (46) is upwardly hooked (50) to contact the upper lip, and the detector detects absence of electrical contact between sensor electrode and a frame (32) hooked behind the lower lip.

6 Claims, 7 Drawing Figures

U.S. Patent    Mar. 31, 1981    Sheet 1 of 2    4,258,709
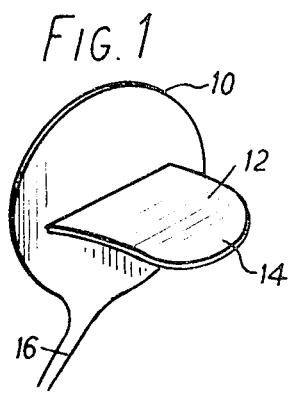
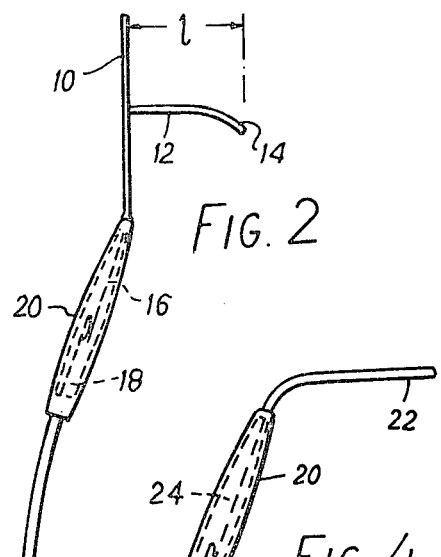
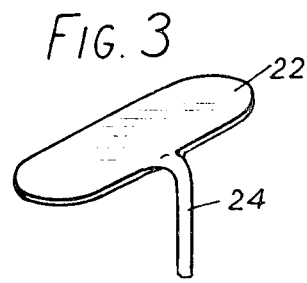
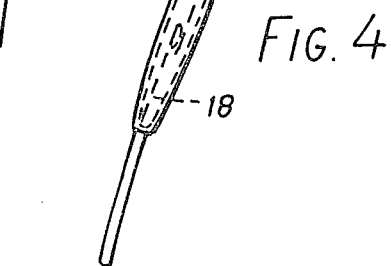
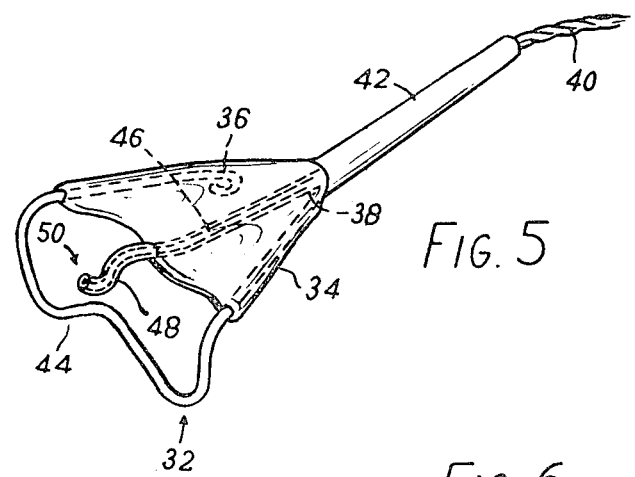
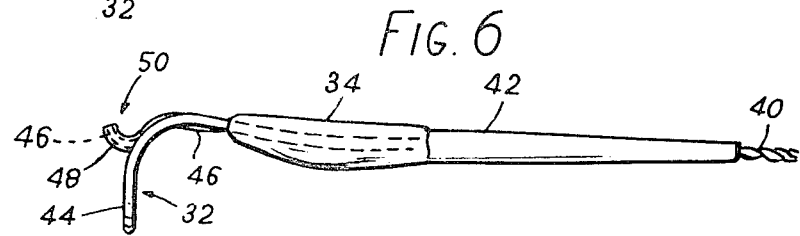

DEVICE TO COMBAT DRIBBLING

BACKGROUND TO THE INVENTION

This invention relates to devices for teaching a patient to keep his lips closed. Such devices are particularly useful to combat a tendency to dribble, for example in patients suffering from certain forms of dysarthria, especially those associated with spasticity; in patients who persistently breathe through their mouths; and in patients who have suffered strokes. It is often possible for such a patient to swallow his saliva provided he can be taught to keep his lips closed.

SUMMARY OF THE INVENTION

The invention provides a device for teaching a patient to keep his lips closed, characterised in that it comprises an electrode adapted for insertion between the patients lips to make electrical contact with at least one of the lips when the lips are closed but not otherwise, electrical detector means arranged to detect when the electrode ceases to make contact with said lip, and an indicator operable by the detector means when such cessation of contact is detected.

In one embodiment, the electrode includes a sheet portion for insertion between the lips, the free end of which may be curved out of the plane of the sheet. The electrode preferably has a backing portion generally perpendicular to the sheet to limit the extent to which the electrode can be inserted between the lips.

The detector means may operate by detecting a change in capacitance and/or resistance between the sensor electrode and a second electrode provided for contacting with another part of the patient's body, on release of the sensor electrode from the patient's lips. The indicator means preferably provides an audible warning on release of the sensor electrode from the patient's lips.

In an alternative form, a frame is provided around the electrode, electrical connection being made between the frame and the electrode when both are inserted between the closed lips of the patient, such connection being broken and detected by the detector means when the patient opens his lips. The frame may have a depending formation to hook behind the lower lip, the electrode being arranged to contact the upper lip when closed.

BRIEF DESCRIPTION OF THE DRAWINGS

In order that the invention may be more clearly understood, three embodiments thereof will now be described by way of example, with reference to the accompanying drawings, wherein:

FIGS. 1 and 3 are perspective views of two sensor electrodes,

FIGS. 2 and 4 are cross-sections through the electrodes of FIS. 1 and 3 respectively, FIG. 5 is a perspective view and FIG. 6 is a side view, of a preferred electrode device.

DESCRIPTION OF PREFERRED EMBODIMENTS

Figure 7:
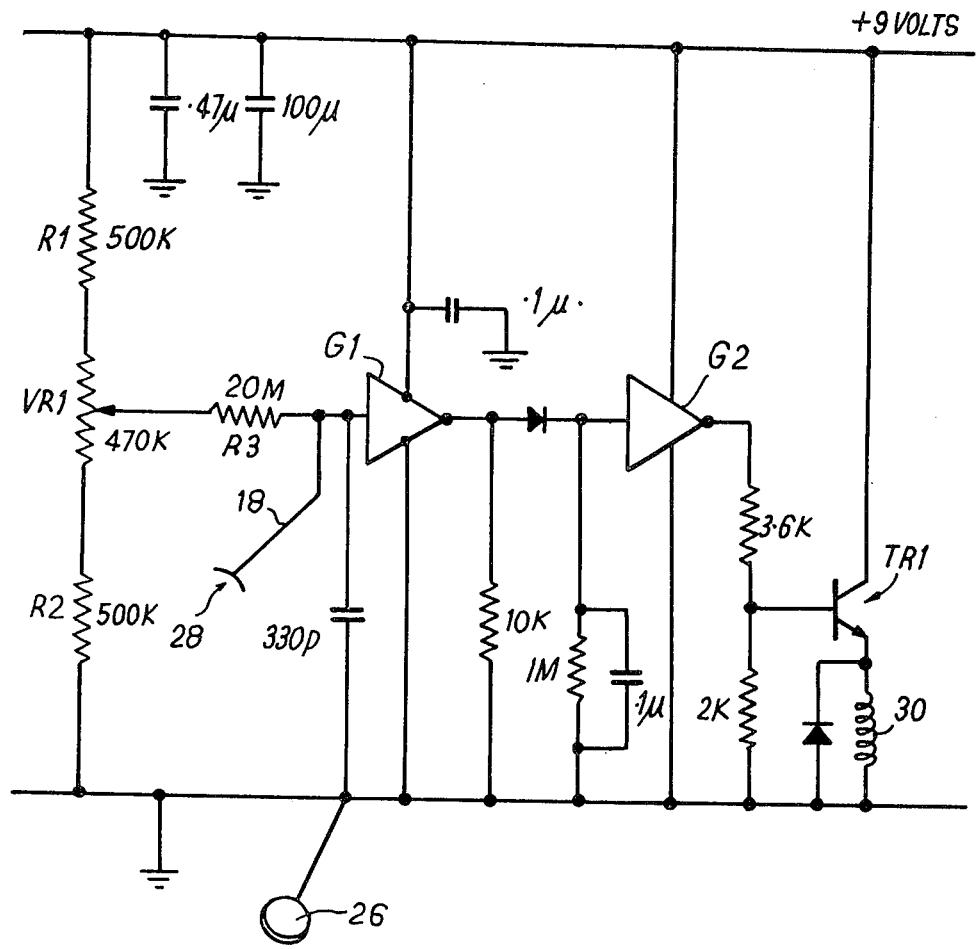
FIG. 7 is a circuit diagram of detector means and indicator means for use with any of the electrodes of FIGS. 1 to 6.

FIGS. 1 and 2 shows a sensor electrode particularly intended for use with spastic patients. It comprises a backing portion in the form of a disc 10, of about 30 mm diameter, although the diameter is not very critical. Extending generally perpendicularly from a mid-portion of the backing disc 10 is a sheet portion in the form of a tongue 12, having a free end portion 14 which is curved downwardly out of the plane of the rest of the tongue. The length 1 of this tongue will vary quite considerably from patient to patient, depending on whether the patient is an adult or a child and on the thickness of his lips. A length is chosen for any given patient such that the tongue 12 can be inserted between the patient's lips and gripped thereby, the backing disc 10 preventing further insertion, and the tongue 12 being sufficiently short that the patient cannot grip the tongue between his teeth. The curved end 14 of the tongue assists the patient in gripping the electrode, because it conforms to a limited extent with the surface of its lower lip inside his mouth.

The backing disc 10 has a tail 16 formed from the same sheet but bent slightly backwardly as seen in FIG. 2. To this tail is soldered a lead wire 18. Insulation 20 is provided around this soldered joint and around the tail 16.

FIGS. 3 and 4 show an alternative sensor electrode, which is intended for more general use than the electrode shown in FIGS. 1 and 2, for example with patients who persistently breathe through their mouths, and/or patients who have suffered strokes. This electrode has no back disc 10, and can therefore be manufactured from a single sheet of stainless steel. It comprises an elongate, generally oval sheet portion 22, wider than its length in the direction of insertion between the lips, typically about 30 mm wide by 10 mm. However, it will be appreciated than the only restriction on the length dimension is that it should be possible for the patient to fit the electrode between his lips comfortably, while in the case of the width dimension the criterion is that the sheet portion 22 shall be sufficiently wide to enable the patient to grip the electrode between his lips, while not being sufficiently wide as to allow the patient easily to grip the electrode between his teeth. One longer edge of the sheet portion 22 has a depending tail 24 to which is soldered a lead 18, and which is provided with insulation 20 in the same manner as the electrode of FIGS. 1 and 2. The depending tail 24 provides a backing portion to assist in preventing the patient from inserting the sheet portion between his teeth, in a somewhat similar manner to the backing disc 10.

The electrodes shown in FIGS. 1 to 4 are fabricated from sheet stainless steel, which is a material which is easy to clean, hygenic and acceptable to the patient. The shape and weight of the sensor electrodes are such that they are not retainable between the lips by any means other than a small but conscious effort to hold them there. It is also unlikely to be possible to accidentally knock the electrode in between the lips so as to damage the teeth or mouth of the patient.

As an alternative material to stainless steel, the electrodes described could be moulded from a synthetic plastics material. A particularly preferred material is acrylic plastics, such as that used in the manufacture of dentures. In this case, when it is moulded the electrode will have a wire embedded in the surface of the tongue 12 or sheet portion 22, to provide a conducting portion of the electrode. So that the electrode has a smooth finished surface (which is necessary in order not to aggravate the patient), the electrode is initially moulded with the wire slightly below the surface of the tongue or sheet portion, and is subsequently exposed by filing or other abrasive removal of material. The wire extends through the tail 16 or 24, and no separate lead wire 18 is needed.

The above electrodes are used in conjunction with a secondary electrode 26 (FIG. 7), which is simply a flat disc of, for example, stainless steel which in use is placed in contact with some portion of the patient's body. Suitably the electrode 26 is slipped inside the patient's waistband, in contact with his skin. The circuitry of FIG. 7 (described later) detects when a circuit between the sensor electrode and the secondary electrode 26 through the patient's body is broken and provides an indication.

FIGS. 5 and 6 shows a preferred sensor electrode device, which does not require a secondary electrode 26. It comprises an outer frame 32 bent from stainless steel wire. The ends 36,38 of the wire of this frame are moulded within a body portion 34 made from acrylic plastics material. The end 36 is merely held in the plastics material, but the end 38 is connected within an insulating sleeve 42 to one wire of a connecting flex 40. The outer frame 36 has a depending W-shaped formation 44, which hooks behind the patient's lower lip and can be bent to give a good fit. We have found that the W formation enhances this fit.

Between the ends 36,38, a sensor electrode 46 is moulded in the body. This electrode is a stainless steel wire with a covering insulating sleeve 48. The sensor electrode 46 is generally in the plane of the frame 32, except that where the frame has the W formation 44, it terminates in an upturned hook 50, which projects slightly above and beyond the frame. The sleeve 48 insulates the entire electrode 46 except that at the very tip of the hook 50 the sleeve terminates flush with the wire of the electrode, leaving the end bare. The sensor electrode 46 is connected within the sleeve 42 to a second wire of the flex 40.

In use, with the W formation hooked behind the patient's lower lip, the bare tip of the hook 50 will contact the patient's upper lip as long as his mouth is closed, giving a circuit passing through his body from the sensor electrode 46 to the frame 32. This circuit is broken if the patient opens his mouth, the hook 50 no longer contacting the upper lip. The electrode device may fall from the patient's mouth, but this is not essential.

FIG. 7 shows a circuit diagram of electronic equipment, together with the secondary electrode 26, which can be ued in conjunction with the electrodes of FIGS. 1 to 4 to detect when a patient has opened his mouth and the sensor electrode has fallen from between his lips. The sensor electrode is designated 28 in FIG. 7. The circuit is arranged to detect changes in capacitance and resistance between the electrodes 26,28 if the electrode 28 falls from between the patient's lips. If this occurs, an indicator in the form of a buzzer 30 is actuated. Visible indicators could be used, but an audible indicator is preferable since it serves as an instant reminder to the patient that he must close his mouth (replacing the sensor electrode 28) and thus the patient is taught to keep his mouth closed, and is prevented from dribbling.

The secondary electrode 26 is connected to earth, while the sensor electrode 28 is connected to an input of an inverter gate G1, providing detector means. The input to the gate G1 is biased by a resistor network comprising resistors R1, R2, R3 and a potentiometer VR1. R1, VR1 and R2 have resistances of about 500K$\Omega$, while R3 has a resistance of 20M$\Omega$, and this means that the current to the input of the gate G1 and passing through the electrode 28 is very small and not noticeable by the patient. Potentiometer VR1 is adjusted such that when the electrode 28 is in the patient's mouth the voltage at the input of gate G1 is just below that necessary to trigger the gate. Consequently the output of gate G1 is at a high level. If the patient drops the electrode 28, the resulting change in capacitance and resistance between the input of gate G1 and earth triggers the gate so that its output falls to a low level. This is communicated to an input of a second similar gate G2, which acts as an inverter and buffer. The output of gate G2 then goes to a high level and turns on a driver transistor TR1 to operate the buzzer 30. When the electrode 28 is replaced between the patient's lips, the buzzer 30 will cease to operate.

When the circuit of FIG. 7 is to be used with the electrode device of FIGS. 5 and 6, the frame 32 is connected in place of the secondary electrode 26, and the sensor electrode 46 is connected in place of the sensor electrode 28, through the flex 40.

The gates G1 and G2 are provided by 1/6 each of a C-MOS integrated circuit type 4049, giving the desired high input impedance. The transistor TR1 is suitably of type 2N1316. However, it will be appreciated that other designs for the detector and indicator circuitry could be used.

We claim:
1. A device for teaching a patient to keep his lips closed, comprising a first electrode; a second electrode in the form of a frame around the first electrode; and means for holding the two electrodes in a spaced relationship; said device being constructed and arranged for insertion between a patient's lips with said first electrode in contact with one of the patient's lips and with said second electrode in contact with the other of said patient's lips to complete an electrical circuit when the patient's lips are closed; electrical detector means for detecting the breaking of said electrical circuit when the lips are opened; and an indicator operably connected to and controlled by the detector for providing an indication when said electrical circuit is broken.

2. A device according to claim 1 wherein the second electrode has a depending portion for hooking behind the patient's lower lip.

3. A device according to claim 2 wherein the first electrode has a portion lying above the second electrode for making contact with the patient's upper lip.

4. A device according to claim 2 wherein the depending formation is W-shaped.

5. A device according to claim 2 wherein said depending portion of said second electrode is bendable to provide a good fit on the patient's lower lip.

6. A device according to claim 1 including an insulating sleeve covering the first electrode to prevent electrical contact with the patient's lower lip, the first electrode having a bared, upwardly hooked tip to contact the patient's upper lip.

* * * * *